United States Patent
Allmendinger et al.

(10) Patent No.: US 9,619,869 B2
(45) Date of Patent: Apr. 11, 2017

(54) IMAGE-BASED MOTION COMPENSATION OF IMAGE DATA

(71) Applicant: Siemens Aktiengesellschaft, Munich (DE)

(72) Inventors: Thomas Allmendinger, Forchheim (DE); Herbert Bruder, Hoechstadt (DE); Thomas Flohr, Uehlfeld (DE); Christopher Rohkohl, Hattingen (DE)

(73) Assignee: Siemens Aktiengesellschaft, Munich (DE)

( * ) Notice: Subject to any disclaimer, the term of this patent is extended or adjusted under 35 U.S.C. 154(b) by 194 days.

(21) Appl. No.: 14/457,215

(22) Filed: Aug. 12, 2014

(65) Prior Publication Data
US 2015/0063534 A1 Mar. 5, 2015

(30) Foreign Application Priority Data

Aug. 30, 2013 (DE) .................. 10 2013 217 351

(51) Int. Cl.
*A61B 6/00* (2006.01)
*G06T 5/00* (2006.01)
(Continued)

(52) U.S. Cl.
CPC .............. *G06T 5/003* (2013.01); *A61B 6/03* (2013.01); *A61B 6/032* (2013.01); *A61B 6/503* (2013.01);
(Continued)

(58) Field of Classification Search
CPC ..... G06T 5/003; G06T 19/20; G06T 2200/04; G06T 2207/10081; G06T 2207/20048;
(Continued)

(56) References Cited

U.S. PATENT DOCUMENTS

2006/0140482 A1* 6/2006 Koehler ............... G06T 11/006
382/193
2011/0142313 A1 6/2011 Claus
(Continued)

FOREIGN PATENT DOCUMENTS

| CN | 1809841 A | 7/2008 |
|---|---|---|
| CN | 102982582 A | 3/2013 |

(Continued)

OTHER PUBLICATIONS

Rohkohl Christopher et al., "Improving best-phase image quality in cardiac CT by motion correction with MAM optimization", in: Medical Physics, vol. 40, No. 3, Mar. 2013, pp. 031901-1 til 031901-15.
(Continued)

*Primary Examiner* — Courtney Thomas
(74) *Attorney, Agent, or Firm* — Harness, Dickey & Pierce, P.L.C.

(57) ABSTRACT

A method, a computer program, a computer program product and a computed tomography system are disclosed. The image data is a spatially three-dimensional reconstruction. At least one value for an image metric of the image data is determined. A motion field for motion compensation of the image data is then determined on the basis of image data as a function of the image metric. Essentially, partial image data is determined, wherein the partial image data corresponds in each case to the spatially three-dimensional reconstruction from scan data of an angular sub-range. The motion field of the image data is determined at the control points via an optimization method as a function of the image metric, so that, thereafter, the partial image data is transformed in accordance with the motion of the motion field. New image data is then produced by merging the partial image data.

19 Claims, 4 Drawing Sheets

(51) Int. Cl.
  *A61B 6/03* (2006.01)
  *G06T 7/00* (2017.01)
  *G06T 19/20* (2011.01)
  *G06T 11/00* (2006.01)

(52) U.S. Cl.
  CPC .......... *A61B 6/5205* (2013.01); *A61B 6/5264* (2013.01); *G06T 7/0012* (2013.01); *G06T 11/005* (2013.01); *G06T 19/20* (2013.01); *A61B 6/4078* (2013.01); *A61B 6/4085* (2013.01); *A61B 6/4441* (2013.01); *A61B 6/481* (2013.01); *A61B 6/482* (2013.01); *A61B 6/507* (2013.01); *A61B 6/5288* (2013.01); *A61B 6/541* (2013.01); *G06T 2200/04* (2013.01); *G06T 2207/10081* (2013.01); *G06T 2207/20048* (2013.01); *G06T 2207/20201* (2013.01); *G06T 2207/20221* (2013.01); *G06T 2211/412* (2013.01); *G06T 2211/416* (2013.01); *G06T 2211/421* (2013.01); *G06T 2211/436* (2013.01)

(58) Field of Classification Search
  CPC . G06T 2207/20201; G06T 2207/20221; G06T 2211/416; G06T 2211/421; A61B 6/503; A61B 6/5264; A61B 6/03

USPC ...................................................... 378/4–20
  See application file for complete search history.

(56) References Cited

U.S. PATENT DOCUMENTS

| 2011/0317901 | A1 | 12/2011 | Allmendinger et al. |
| 2012/0275656 | A1 | 11/2012 | Boese et al. |
| 2013/0077843 | A1 | 3/2013 | Bruder et al. |

FOREIGN PATENT DOCUMENTS

| CN | 103190927 A | 7/2013 |
| CN | 103198497 A | 7/2013 |
| DE | 102010024684 A1 | 12/2011 |
| DE | 102011017710 A1 | 10/2012 |
| DE | 102011075287 A1 | 11/2012 |
| DE | 102011083641 A1 | 3/2013 |
| DE | 102011083643 A1 | 3/2013 |

OTHER PUBLICATIONS

DE Office Action for DE 102013217351.2 dated Apr. 24, 2014.
First Office Action issued on Sep. 29, 2016 by the Chinese Patent Office for Chinese Patent Application No. 2014104297708.

\* cited by examiner

IMAGE-BASED MOTION COMPENSATION OF IMAGE DATA

PRIORITY STATEMENT

The present application hereby claims priority under 35 U.S.C. §119 to German patent application number DE 102013217351.2 filed Aug. 30, 2013, the entire contents of which are hereby incorporated herein by reference.

FIELD

At least one embodiment of the invention generally relates to a method, a computer program, a computer program product and/or a computed tomography system for motion compensation of image data.

BACKGROUND

Computed tomography is an imaging technique that is used primarily for medical diagnostics and material analysis. In computed tomography, a radiation source and, acting in conjunction therewith, a radiation detector rotate around a scanned object to obtain spatially three-dimensional image data. During the rotational movement, scan data is acquired within an angular range. The scan data is a plurality of projections containing information about the attenuation of the radiation by the object. The scan data is also known as raw data. From this scan data, the image data can then be reconstructed, e.g. using so-called filtered back projection or an iterative reconstruction method. If the object moves during scanning, the motion may produce blurring and artifacts in the reconstruction of the image data.

Thus it is well known that cardiac motion during a CT scan can produce inconsistent and motion-artifact-impaired image data. As a result, the clinical usefulness of the image data is severely limited. To prevent motion artifacts, modern tomographic cardiac imaging uses phase-related acquisition of scan data by means of retrospective or prospective triggering. Thus in the case of prospective triggering, only data in a certain time interval around the resting phase of the heart cycle is acquired and used for image reconstruction. The common objective of these approaches is to "freeze" cardiac motion in order to reduce data inconsistency and therefore increase image quality.

An approach for increasing the image quality for a partially and cyclically moving object is known from the publication DE 10 2011 083 643 A1. There, a method for determining a motion field in an image domain of a CT image dataset is disclosed. A projection dataset of a CT system is determined for a predefined motion phase and a range of projection angles. In addition, the motion field is iteratively determined by minimizing a cost function of CT image datasets of a first image resolution using a first analytical reconstruction algorithm, the cost function being based on raw data or transformed into the image domain and the data sets being reconstructed in a motion-compensating manner using motion fields.

SUMMARY

At least one embodiment of the invention specifies how motion compensation of image data of a moving object being scanned can be carried out on the basis of image data.

A method, a computer program, computer program product, a computer and a computed tomography system are disclosed.

Cited features, advantages or alternative embodiments apply equally to the other claimed subject matters and vice versa. In other words, the concrete claims relating to a system, for example, can also be further developed using the features described or claimed in connection with a method. The corresponding functional features of the method are implemented by corresponding concrete modules.

At least one embodiment of the invention relates to a method for motion compensation of image data of a moving scanned object. The image data is a spatially three-dimensional reconstruction from scan data, wherein the scan data was acquired during a relative rotational movement between a radiation source and the scanned object within an angular range. This angular range comprises a plurality of angular sub-ranges, wherein each angular sub-range is assigned to a temporal control point. In particular, the temporal control point can be a time that is defined by the time interval during which scan data was acquired within the respective angular sub-range. The core of the invention is the following iterative method. During a first step of the method according to the invention, at least one value for an image metric L of the image data is determined, the image metric being a measure of motion artifacts in the image data. The inventors have now discovered that a motion field s for motion compensation of the image data can be determined on the basis of image data as a function of the image metric, wherein the motion field is a measure of the motion of the image data. For this purpose, in a second step, partial image data is determined, wherein the partial image data corresponds in each case to the spatially three-dimensional reconstruction from scan data of an angular sub-range. In a third step, the motion field s of the image data is determined at the control points by means of an optimization method as a function of the image metric, so that, in a fourth step, the partial image data can be transformed in accordance with the motion described by the motion field. In the fifth step, new image data is produced by merging the partial image data. These steps of the iterative method are carried out until a stop criterion is reached. The new image data is motion-compensated by the transformation of the transformed partial image data and has an improved image quality compared to the original image data. Due to the fact that the method is inventively carried out in an image-based manner, it requires less computational complexity than other raw-data-based methods and can in particular be carried out on a so-called workstation and independently of a reconstruction computer. The method according to an embodiment of the invention therefore proves particularly practical for clinical practice.

An embodiment of the invention also relates to a computer program having program code for carrying out all the inventive method steps of an embodiment when the computer program is run on a computer. By way of a computer program according to an embodiment of the invention, the method according to an embodiment of the invention can be executed quickly, reliably and reproducibly.

An embodiment of the invention also relates to a computer program product in the form of a machine-readable medium on which the computer program is retrievably stored. The storage of the computer program on a machine-readable medium allows the method according to an embodiment of the invention to be run in a technically simple manner and reproducibly on different computers.

An embodiment of the invention likewise relates to a computer for image processing, comprising a memory for storing computer programs and a processor for executing the stored computer programs, said memory holding a computer program which carries out the method according to an embodiment of the invention when the computer program is run on the computer.

An embodiment of the invention additionally relates to a computed tomography system, comprising a radiation source and a radiation detector interacting with the radiation source, designed to acquire scan data during a relative rotational movement between the radiation source and a scanned object within an angular range, also comprising a reconstruction unit, designed to reconstruct image data from the scan data, further comprising an embodiment of an inventive processing unit for image processing.

BRIEF DESCRIPTION OF THE DRAWINGS

The invention will now be described and explained in greater detail with reference to the example embodiments illustrated in the accompanying drawings, in which.

DETAILED DESCRIPTION OF THE EXAMPLE EMBODIMENTS

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Before discussing example embodiments in more detail, it is noted that some example embodiments are described as processes or methods depicted as flowcharts. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Methods discussed below, some of which are illustrated by the flow charts, may be implemented by hardware, software, firmware, middleware, microcode, hardware description languages, or any combination thereof. When implemented in software, firmware, middleware or microcode, the program code or code segments to perform the necessary tasks will be stored in a machine or computer readable medium such as a storage medium or non-transitory computer readable medium. A processor(s) will perform the necessary tasks.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

In the following description, illustrative embodiments may be described with reference to acts and symbolic representations of operations (e.g., in the form of flowcharts) that may be implemented as program modules or functional processes include routines, programs, objects, components, data structures, etc., that perform particular tasks or implement particular abstract data types and may be implemented using existing hardware at existing network elements. Such existing hardware may include one or more Central Processing Units (CPUs), digital signal processors (DSPs), application-specific-integrated-circuits, field programmable gate arrays (FPGAs) computers or the like.

Note also that the software implemented aspects of the example embodiments may be typically encoded on some form of program storage medium or implemented over some type of transmission medium. The program storage medium (e.g., non-transitory storage medium) may be magnetic (e.g., a floppy disk or a hard drive) or optical (e.g., a compact disk read only memory, or "CD ROM"), and may be read only or random access. Similarly, the transmission medium may be twisted wire pairs, coaxial cable, optical fiber, or some other suitable transmission medium known to the art. The example embodiments not limited by these aspects of any given implementation.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

At least one embodiment of the invention relates to a method for motion compensation of image data of a moving scanned object. The image data is a spatially three-dimensional reconstruction from scan data, wherein the scan data was acquired during a relative rotational movement between a radiation source and the scanned object within an angular range. This angular range comprises a plurality of angular sub-ranges, wherein each angular sub-range is assigned to a temporal control point. In particular, the temporal control point can be a time that is defined by the time interval during which scan data was acquired within the respective angular sub-range. The core of the invention is the following iterative method. During a first step of the method according to the invention, at least one value for an image metric L of the image data is determined, the image metric being a measure of motion artifacts in the image data. The inventors have now discovered that a motion field s for motion compensation of the image data can be determined on the basis of image data as a function of the image metric, wherein the motion field is a measure of the motion of the image data. For this purpose, in a second step, partial image data is determined, wherein the partial image data corresponds in each case to the spatially three-dimensional reconstruction from scan data of an angular sub-range. In a third step, the motion field s of the image data is determined at the control points by means of an optimization method as a function of the image metric, so that, in a fourth step, the partial image data can be transformed in accordance with the motion described by the motion field. In the fifth step, new image data is produced by merging the partial image data. These steps of the iterative method are carried out until a stop criterion is reached. The new image data is motion-compensated by the transformation of the transformed partial image data and has an improved image quality compared to the original image data. Due to the fact that the method is inventively carried out in an image-based manner, it requires less computational complexity than other raw-data-based methods and can in particular be carried out on a so-called workstation and independently of a reconstruction computer. The method according to an embodiment of the invention therefore proves particularly practical for clinical practice.

According to another aspect of an embodiment of the invention, the angular range is the minimum angular range required for a tomographically complete reconstruction. In such a case, the angular range is given by $180°+\phi$, where $\phi$ denotes the fan angle, i.e. the opening angle of the fan beam emitted by the radiation source in the radial direction.

According to another aspect of an embodiment of the invention, the partial image data is determined by first performing Fourier transformation of the image data into the frequency domain, then masking the image data by way of a filter function, and reconverting the masked frequency spectrum to the spatial domain by way of Fourier transformation. An advantage of this aspect of an embodiment of the invention is that the partial image data can be determined with low computational complexity and without accessing the raw data.

According to another aspect of an embodiment of the invention, the partial image data is determined in each case by means of forward projection of the image data and subsequent back projection of part of the projected image data corresponding to an angular sub-range. This aspect of the invention can also be carried out with low computational complexity and without accessing the raw data.

According to another aspect of an embodiment of the invention, forward projection of the image data with subsequent motion-compensated back projection by way of the motion field is performed during and/or after carrying out the iterative method. This aspect provides extremely distortion-free motion compensation of the image data so that particularly high image quality is achieved.

According to another aspect of an embodiment of the invention, the image data is the image data of a segmented object. As a result, only the region in the image data whose motion is to be corrected needs to be segmented, so that the image metric is a particularly indicative measure of the motion to be corrected. In addition, the image data then comprises fewer pixels or more specifically voxels, so that the volume of data to be processed is reduced and the method according to an embodiment of the invention can be carried out more quickly and with less computational complexity.

According to another aspect of an embodiment of the invention, the object being scanned is at least one part of a heart and/or at least one coronary vessel. Motion compensation is particularly important for imaging of the heart or more specifically of the coronary vessels, as these are rapidly moving objects and a particularly high spatial and temporal resolution is desirable for interpreting the image data of the heart or more specifically of coronary vessels.

According to another aspect of an embodiment, the value of the image metric is determined for individual image slices from the image data, because the image metric is particularly indicative for those image slices in whose capture area motion actually occurred. Determining values of the image metric for individual image slices is generally more sensitive to motion artifacts than determining a single value of the image metric for the entire set of image data.

According to another aspect of an embodiment of the invention, the image metric is the entropy, the positivity, the compressibility or the total variation of the image data, because these parameters are in each case a good measure of motion artifacts.

According to another aspect of an embodiment of the invention, the optimization method for determining the motion field is a gradient descent method, wherein the gradients $\partial L(s)/\partial s$ are determined in an image-based manner.

According to another aspect of an embodiment of the invention, the motion field for transforming the partial image data is interpolated between the control points. As a result, the motion field can be determined for a large number of time instants, thus enabling image data or more specifically partial image data to be transformed in a particularly precise manner.

An embodiment of the invention also relates to a computer program having program code for carrying out all the inventive method steps of an embodiment when the computer program is run on a computer. By way of a computer program according to an embodiment of the invention, the method according to an embodiment of the invention can be executed quickly, reliably and reproducibly.

An embodiment of the invention also relates to a computer program product in the form of a machine-readable medium on which the computer program is retrievably stored. The storage of the computer program on a machine-readable medium allows the method according to an embodiment of the invention to be run in a technically simple manner and reproducibly on different computers.

An embodiment of the invention likewise relates to a computer for image processing, comprising a memory for storing computer programs and a processor for executing the stored computer programs, said memory holding a computer program which carries out the method according to an embodiment of the invention when the computer program is run on the computer.

An embodiment of the invention additionally relates to a computed tomography system, comprising a radiation source and a radiation detector interacting with the radiation source, designed to acquire scan data during a relative rotational movement between the radiation source and a scanned object within an angular range, also comprising a reconstruction unit, designed to reconstruct image data from the scan data, further comprising an embodiment of an inventive processing unit for image processing.

Figure 1:
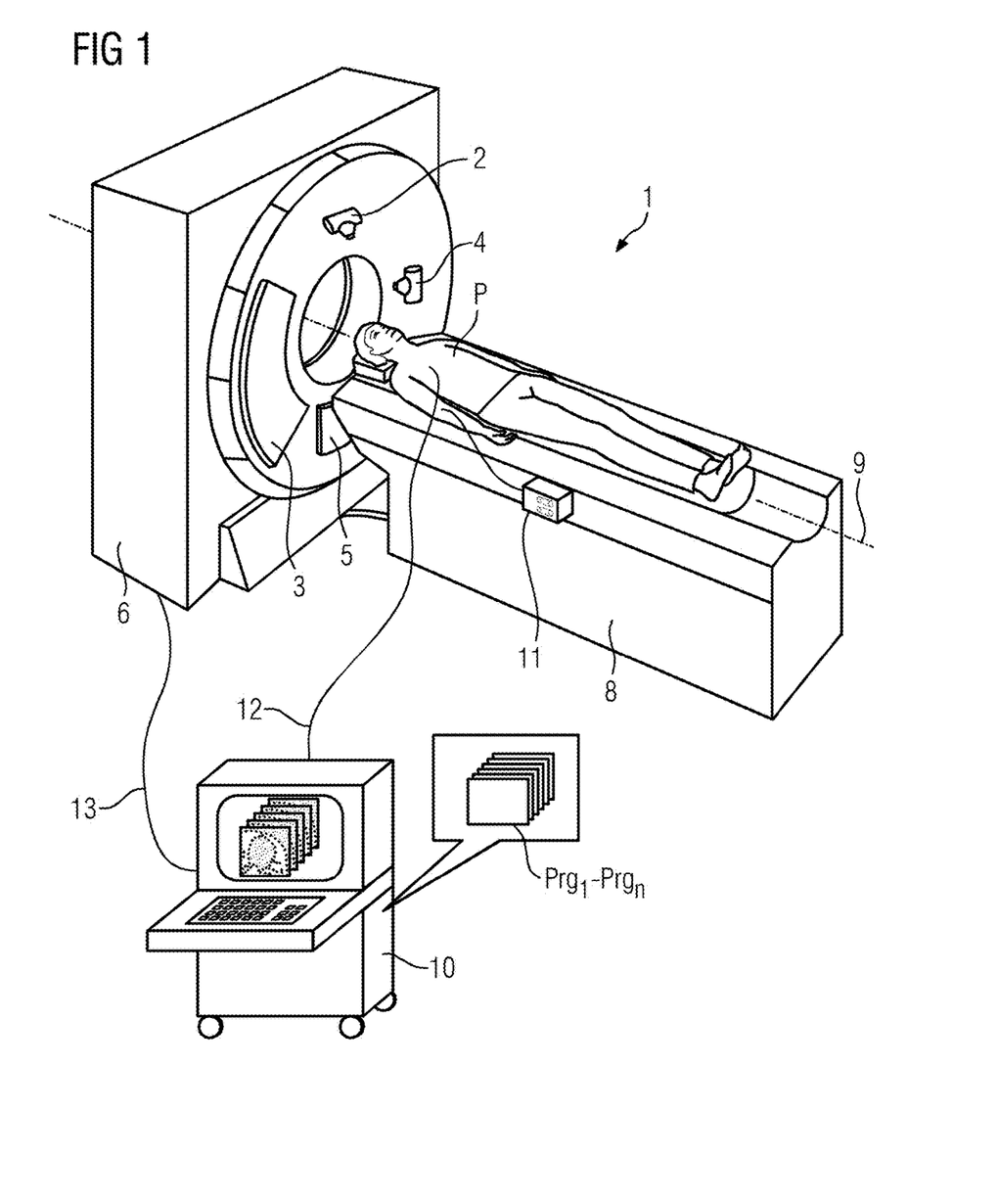
FIG. 1 shows a computed tomography system according to an embodiment of the invention, comprising a CT scanner.
Figure 2:
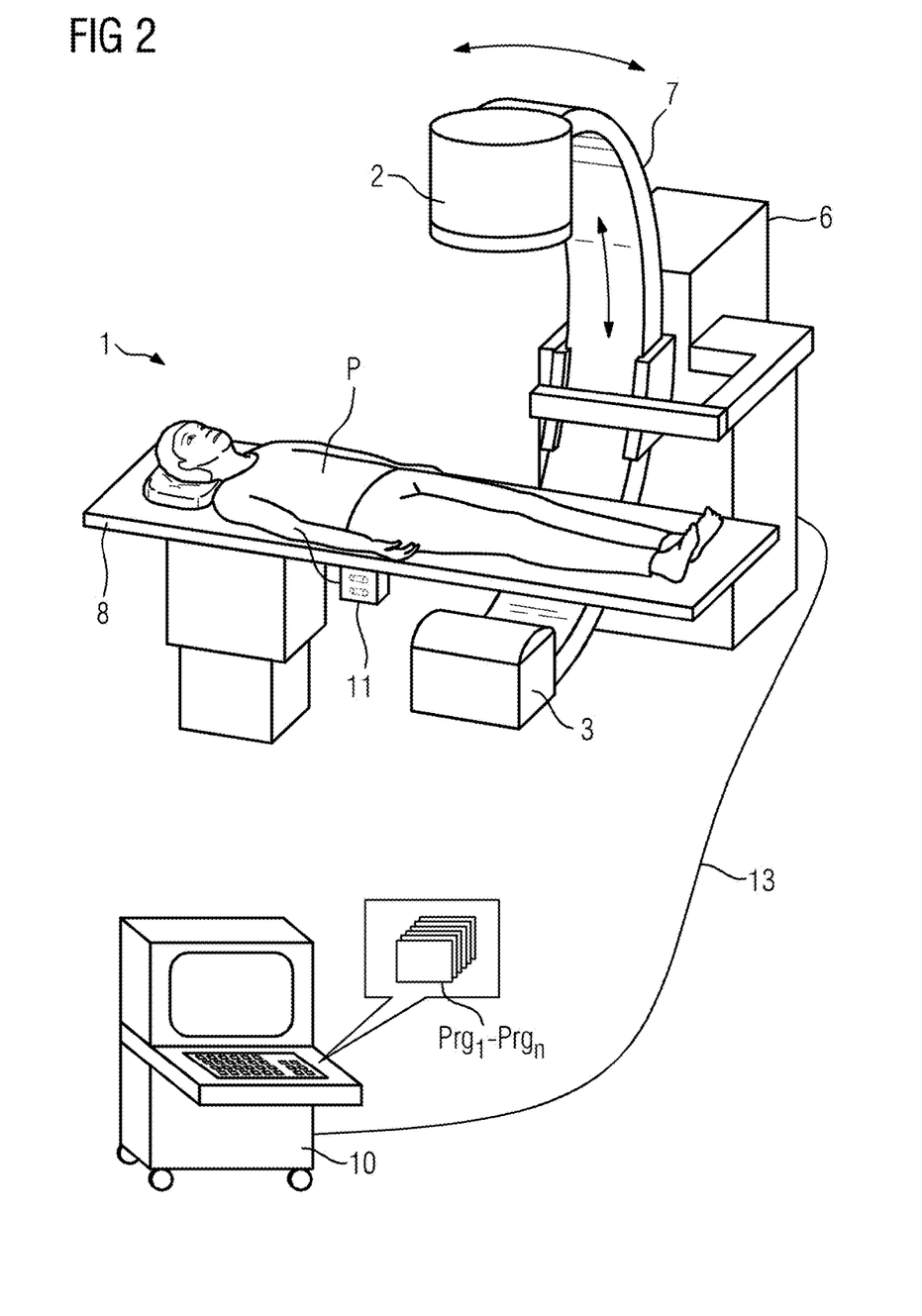
FIG. 2 shows a computed tomography system according to an embodiment of the invention, comprising a C-arm X-ray machine.

FIG. 1 and FIG. 2 show in each case a computed tomography system 1 according to an embodiment of the invention. In the examples shown here, a patient P lies on a patient table 8 during the acquisition of scan data MEAS. The patient table 8 is designed to traverse the patient P along a system axis 9 during a scan. During the acquisition of scan data MEAS, a radiation source 2 and a radiation detector 5 interacting with the radiation source 2 rotate about the system axis 9. The radiation source 2 emits radiation such that this radiation is always detectable to the radiation detector 5. The radiation is attenuated by the respective scanned object, in particular by absorption and reflection of the radiation. In the examples shown here, the scan data MEAS is a plurality of projections of a body part of the patient P, the projections in each case representing the attenuation of the radiation by the body part of the patient P.

In the case of the example embodiment comprising a CT scanner as shown in FIG. 1, the X-ray detector is a detector having a plurality of rows and columns, whereas the C-arm X-ray machine shown in FIG. 2 has an X-ray detector in the form of a flat-panel detector. In each case the X-ray detectors can be implemented both as scintillation counters and as directly converting X-ray detectors. They can also be implemented as counting X-ray detectors which are designed to detect and count individual photons. In the example shown in FIG. 1, the CT scanner additionally has two pairs of interacting radiation sources 2,4 in the form of X-ray tubes, and of radiation detectors 5,4 in the form of X-ray detectors. As a result, the CT scanner shown here is particularly suitable for multi-energy scans in which the two X-ray tubes each emit X-ray radiation having a different energy spectrum. In other embodiments not shown here, the CT scanner of a computed tomography system 1 according to the invention only has one X-ray tube as a radiation source and one X-ray detector as a radiation detector. In the case of a CT scanner, the X-ray tube and X-ray detector are incorporated into the gantry 6. In the case of a C-arm X-ray machine, the X-ray tube and the X-ray detector are connected by a C-arm 7 which is in turn fixed to a gantry 6. The gantry 6 of the CT scanner can be designed to tilt about at least one axis perpendicular to system axis 9. The C-arm 7 of the X-ray machine shown in FIG. 2 can be swiveled or rather rotated along the two arrows.

In addition, the computed tomography systems 1 represented here also have a contrast agent injector 11 for injecting contrast agent into the bloodstream of the patient P. As a result, the scan data MEAS can be acquired using a contrast agent such that e.g. the vessels of the patient P, in particular the ventricles of the beating heart, can be represented with higher contrast in the image data F. Moreover, the contrast agent injector 11 also makes it possible to carry out perfusion measurements for which the proposed method is likewise suitable. Contrast agents are to be understood as meaning substances which enhance the representation of structures and functions of the body in medical imaging. In the context of the present application, contrast agents are to be understood as meaning both conventional contrast agents such as iodine, for example, and tracers such as $^{18}$F, $^{11}$C or $^{13}$N, for example.

A computed tomography system according to an embodiment of the invention also comprises a computer 10 which is also termed a workstation. The computer 10 shown here is designed to control the individual units of the computed tomography system, e.g. to control the patient table 8, the contrast agent injector 11 and the X-ray tube and X-ray detector. The computer 10 is connected to an output unit and an input unit. The output unit is, for example, one (or more) LCD, plasma or OLED screen(s). The output on the output unit comprises, for example, a graphical user interface or the output of image data. The input unit is designed for inputting data, e.g. patient data and to enter and select parameters for the individual units of the computed tomography system. The input unit is, for example, a keyboard, a mouse, a so-called touchscreen or even a microphone for voice input.

In the examples shown here, the computer 10 is also designed to receive the scan data MEAS by means of a data connection from the CT scanner or C-arm X-ray machine, as the case may be, and to reconstruct the image data F from the scan data MEAS by way of a reconstruction unit. In an alternative embodiment of the invention, the computer 10 is connected to a processing system in the form of a reconstruction computer to which the scan data MEAS can be fed by another data connection so that the processing system can reconstruct image data F from the scan data MEAS by way of a reconstruction unit. In particular, said computer 10 can act as a client and the processing system as a server. In a variant of this alternative embodiment, the computer 10 does not have a reconstruction unit and is not designed to reconstruct scan data MEAS into image data F. Irrespective of whether the reconstruction unit is implemented as part of the local computer 10 or as part of a separate processing system, possibly acting as a server, the reconstruction unit can be realized in both software and hardware.

The computer 10 additionally comprises a memory for storing computer programs $Prg_1$-$Prg_n$ and a processor for executing the stored computer programs $Prg_1$-$Prg_n$. In the embodiment shown here, in the memory at least one computer program is stored which carries out all the steps of the method according to an embodiment of the invention when the computer program is run on the computer 10. The computer program for carrying out the method steps of the method according to an embodiment of the invention comprises program code. The computer program can also be implemented as an executable file and/or be stored on a processing system other than the computer 10. For example, the computed tomography system 1 can be designed such that the computer 10 loads the computer program for carrying out the method according to an embodiment of the invention into its internal memory via an intranet or via the Internet. The computer program can also be retrievably stored on a computer program product in the form of a machine-readable medium. In particular, the machine-readable medium can be a CD, DVD, Blu-ray disc, a memory stick or a hard drive.

In addition, the computer 10 in the embodiment shown in FIG. 1 is designed to receive EKG signals of the patient P using an EKG data connection 12 and to process them. By way of the EKG signals received, the computer 10 is in particular designed, as part of so-called prospective triggering, to define the start point of acquisition of scan data MEAS and to start the corresponding scan at the defined time. In addition, the computer 10 is designed, as part of so-called retrospective triggering, to use only part of the acquired projections for reconstruction of image data F and/or provide information about the cardiac phase, which simplifies further processing of already reconstructed image data. A typical field of application of an embodiment of the present invention is the imaging of the heart and/or of the coronary vessels. The scanned object of an embodiment of the inventive method described below can therefore in particular include the beating heart of a patient P and/or at least one coronary vessel.

Figure 3:
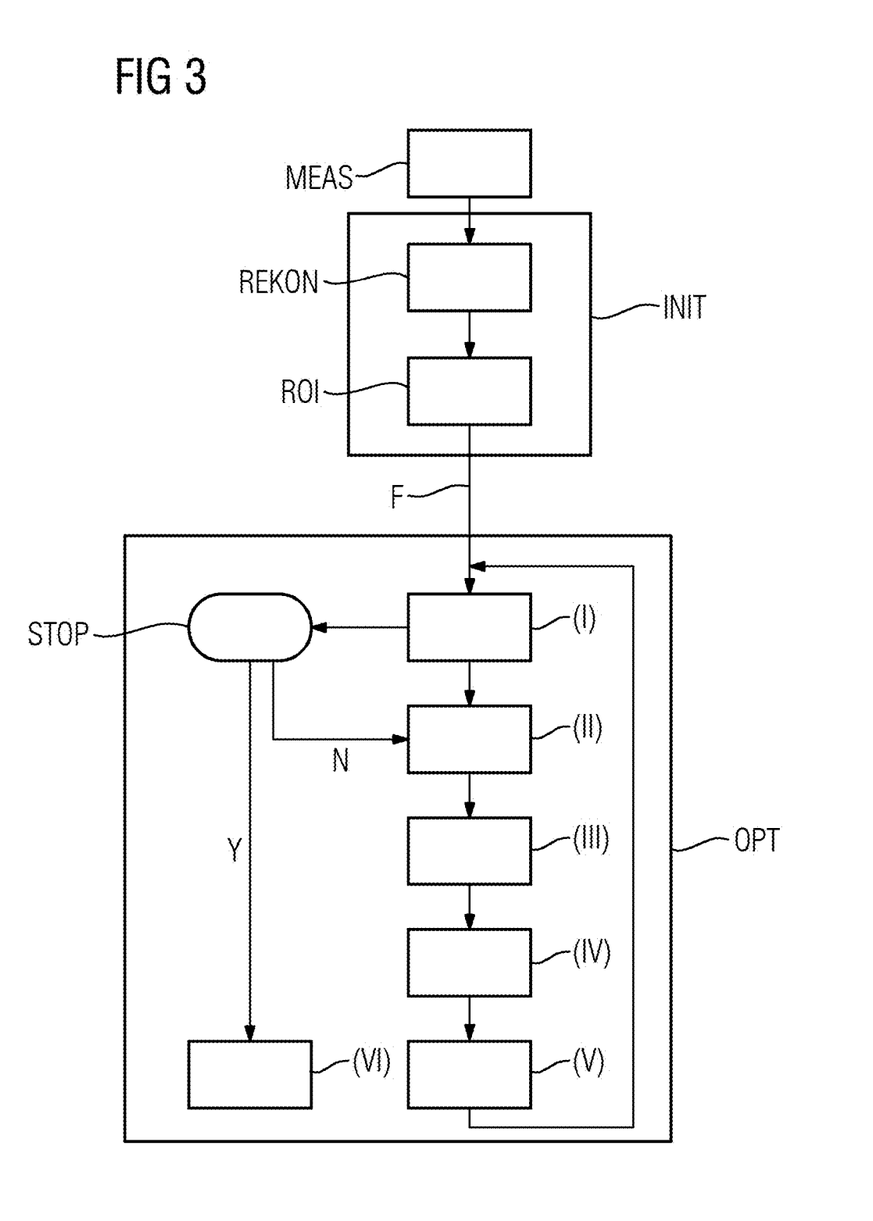
FIG. 3 shows a block diagram of the method according to an embodiment of the invention.

FIG. 3 shows a block diagram of the method according to an embodiment of the invention. The method according to an embodiment of the invention is preceded by the acquisition of the scan data MEAS during a relative rotational movement between a radiation source 2 and the scanned object within an angular range $\Omega$. In the embodiment of the invention shown in FIG. 1, the angular range $\Omega$ extends perpendicularly with respect to the system axis 9. It is well known that a set of scan data MEAS for the spatially three-dimensional reconstruction of image data needs to have been acquired across an angular range $\Omega$ of 180°+$\phi$ in order to satisfy the completeness criterion. Here $\phi$ denotes the fan angle, i.e. the opening angle of the fan beam in the radial direction. In the case of C-arm X-ray machines, instead of fan, the term cone of X-ray radiation is often used which, however, also possesses a defined opening angle $\phi$. Essentially, the invention can be based on the reconstruction REKON of both complete and incomplete scan data MEAS. In particular, the angular range can be greater than, less than or equal to 180°+$\phi$. The angular range $\Omega$ will typically be a continuous angular range. However, it is also conceivable for the method according to the invention to be carried out using a discontinuous angular range $\Omega$, e.g. because the individual parts of the angular range $\Omega$ each correspond to the resting phase of the heart as the scanned object.

The angular range $\Omega$ can be subdivided into a plurality of angular sub-ranges $\omega\_j$. If the scan data MEAS is acquired in an angular range $\Omega$=360°, this can be subdivided into 20 angular sub-ranges with j=1, 2 . . . 20, where $\omega\_j$=18°. Each angular sub-range $\omega\_j$ can now be assigned a temporal control point t_j. For example, the temporal control point t_j is the temporal focus or the start or end of the time interval in which the projections associated with the respective angular sub-range $\omega\_j$ were acquired. If the acquisition of the scan data MEAS takes one second, for example, the spacing between the different temporal control points for 20 equidistant angular sub-ranges $\omega\_j$, with the scanning speed remaining the same, is 50 ms. Of course another number of angular sub-ranges $\omega\_j$ or rather temporal control points t_j can be selected. In addition, in other embodiments of the invention the angular sub-ranges $\omega\_j$ or rather temporal control points t_j can be non-equidistant.

During initialization INIT of an embodiment of the inventive method described here, spatially three-dimensional reconstruction RECON of the image data F from the scan data MEAS takes place. In addition, as part of initialization INIT a so-called region of interest ROI in the image data F can be determined. By selecting a region of interest ROI, the amount of image data F can be reduced so that the method according to an embodiment of the invention can be carried out more quickly and with less computational complexity. In addition, motion artifacts can be determined more sensitively in a selected image region. The region of interest ROI can be determined, for example, by segmenting the image data F. In such a case, the image data F is to be understood in the following as meaning segmented image data. In particular, the area under examination, i.e. the heart and/or a coronary vessel of a patient P, for example, in the image data F can be segmented as a region of interest ROI.

The optimization OPT is iterative and comprises, for each iteration, a plurality of steps with the aim of determining a motion field s of the image data F in an image-based manner, namely by way of an image metric L, wherein the image metric L is a measure of motion artifacts in the image data F. The motion field s indicates a motion of individual picture elements, e.g. of voxels or pixels, within the image domain and can also be described as a vector field. As the motion field s is to be determined at the control points t_j, the motion field s can be in particular a four-dimensional vector field having three spatial components and one temporal component. The dependence on the temporal component, where it is not necessary for understanding, is omitted in the following. The image metric is, for example, the entropy, the positivity, the compressibility or the total variation of the image data F. The entropy of an image is given, for example, by:

$$L(s) = -\sum_h P(h, s) \ln P(h, s), \quad (1)$$

where P(h,s) is the probability of a voxel having the intensity, e.g. in the form of the Hounsfield unit, h within the image data F. The probability distribution P(h,s) can be calculated using different methods familiar to persons skilled in the art. In the first step (i) of the optimization OPT, a value for an image metric L of the image data F is determined. The value of the image metric can either be determined with reference to complete reconstructed volumes of the image data F. Alternatively, a plurality of values of the image metric L can be determined for sub-volumes, in particular in the form of individual image slices, from the image data F. If a plurality of values of the image metric L are determined, these can be combined for the purpose of optimization OPT, e.g. by addition of the values.

In a further step (ii) of optimization OPT, partial image data f_j is determined, wherein the partial image data corresponds in each case to the spatially three-dimensional reconstruction from scan data of an angular sub-range ω_j. The scan data acquired during the relative rotational movement between radiation source 2 and scanned object within an angular sub-range ω_j will hereinafter also be referred to as partial scan data MEAS_j. An assigned angular sub-range ω_j and assigned partial scan data MEAS_j exist for each temporal control point t_j. However, according to the invention no reconstruction of raw data takes place in step (ii), but only partial image data f_j is determined which corresponds to reconstruction from the partial scan data MEAS_j. As a result, the method according to the invention can be implemented in an image-based manner and therefore particularly quickly and with comparatively low computational complexity. Such determination of partial image data f_j can take place, for example, by means of Fourier transformation, as will be explained in greater detail in the description for FIG. 4. The partial image data f_j can also be determined using forward projection of the image data F and subsequent back projection of part of the projected image data F corresponding to an angular sub-range ω_j.

In a further step (iii) of optimization OPT, a motion field s of the image data F at the control points t_j is determined as a function of the image metric L using an optimization method. In particular, optimization OPT can be carried out such that the value of the image metric is optimized. In other words, optimization OPT can encompass the value of the image metric tending toward an extreme value, in particular a maximum or a minimum, but without necessarily reaching the extreme value. Basically, a wide variety of optimization methods suitable for this purpose can be used to implement the invention. Here the invention will be described in greater detail using the example of the gradient descent method. In each iteration k the motion field s is described by the following formula (1), where τ is a parameter to be determined:

$$s^{k+1} = s^k - \tau^k \frac{\partial L(s^k)}{\partial s^k} \quad (1)$$

As an initial value for the first iteration, basically any field can be selected, in particular a field whose entries are all 0. The gradients $$\frac{\partial L(s^k)}{\partial s^k}$$

are determined in an image-based manner. As the motion field for the control points t_j is to be determined, the gradients $$\frac{\partial L(s^k)}{\partial s^k} = \frac{\partial L}{\partial F} \frac{\partial F}{\partial s_j^k}$$

are required. For simplification, the iteration superscript k will be omitted in the following. The new, iteratively generated image data F can be represented as a superposition, in particular as the sum, of the partial image data f_j. Using the three-dimensional position vector x, we get:

$$\frac{\partial F(x, s)}{\partial s_j} = \sum_j \frac{\partial f_j(x, s)}{\partial s_j} \quad (3)$$

The gradients $$\frac{\partial f_j(x, s)}{\partial s_j}$$

can in particular be calculated as difference quotients, so that we obtain the expression $$\frac{\partial f_j(x, s)}{\partial s_j} = f_j(x + s + e) - f_j(x + s)$$

with the three-dimensional unity vector e.

In a further step (iv) of optimization OPT, the partial image data f_j is transformed according to the movement described by the motion field s. Such a transformation takes place by shifting, in the k+1th iteration step, picture elements such as pixels or voxels of the individual partial image data f_j of the kth iteration step according to the motion field s. The transformation can therefore also include a shifting of intensity values of the partial image data f_j in the three-dimensional image domain. In addition, the transformation of the partial image data f_j can also include interpolation of the partial image data f_j. In one embodiment of the invention, the motion field s is also interpolated, because according to the method described hitherto, the motion field is only defined at the discrete temporal control points t_j.

In a further step (v) of optimization OPT, new image data F is generated by merging, in particular by summation, of the transformed partial image data f_j. In one embodiment of the invention, an iteration k ends after step (v) and the next iteration k+1 is initiated with step (i), wherein the newly merged image data replaces the original image data. In addition, the optimization OPT includes the query STOP of a stop criterion. Basically the query STOP can be carried out between or during each of the steps (i) to (v) described here. For example, the query STOP can include whether a certain maximum number k_max of iterations has been run through, or whether the value of the metric has changed by less than a limit value between two successive iterations. The query STOP step can also include the interrogation of a plurality of stop criteria. In the example shown in FIG. 3, the stop criterion is interrogated after step (i). If the stop criterion is fulfilled Y, the process continues with step (vi), if the stop criterion is not fulfilled N, the process continues with step (ii).

Step (vi) comprises the forward projection of the image data F with subsequent motion-compensated back projection by means of the motion field s. Motion-compensated back projection enables interpolation of the partial image data f_j to be dispensed with, so that the quality of image data F produced by means of step (vi) is particularly high. It is therefore particularly advantageous to carry out this step at the end of the iterative optimization OPT. However, step (vi) can also be carried out repeatedly during the optimization OPT, e.g. in order to output a visual intermediate result of the optimization OPT.

Figure 4:
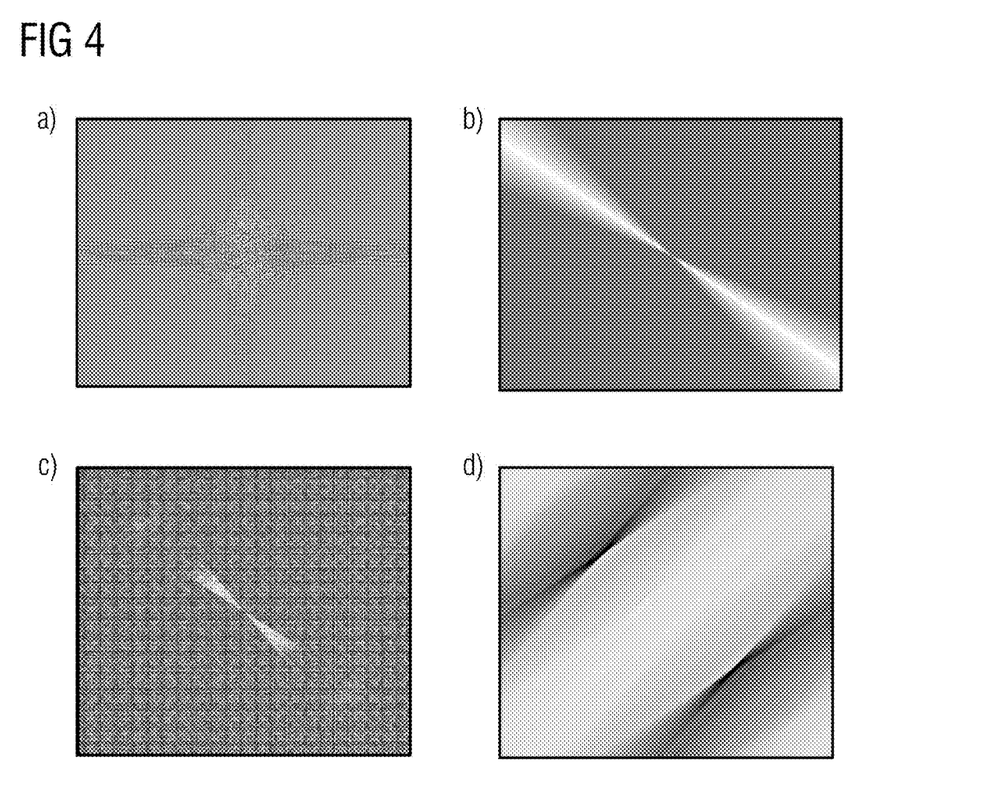
FIG. 4 shows an illustration of determining partial image data by way of Fourier transformation.

FIG. 4 shows an illustration of determining partial image data by means of Fourier transformation. A tomographic reconstruction is based on the summation of projections. According to the so-called Fourier slice theorem, the Fourier transformation of a projection is identical to the one-dimensional Fourier spectrum of the attenuation distribution in the selected projection direction. FIG. 4a) shows the two-dimensional Fourier spectrum of two-dimensional image data F. The Fourier spectrum shown here is therefore a spectrum of spatial frequencies, wherein the brightness of the intensity acts in the frequency domain. FIG. 4b) shows the mask which is used in the example discussed here to mask the frequency spectrum of the image data F using a filter function. As the time of acquisition of the individual projections is known, a temporal order of the one-dimensional Fourier spectra calculated according to the Fourier slice theorem can also be determined. The mask or more specifically the filter function fulfills the purpose of selecting a sector from the Fourier spectrum, wherein a sector corresponds to an angular sub-range ω_j. The mask or more specifically the filter function is therefore also termed directional. FIG. 4c) shows the masked or rather filtered Fourier spectrum. According to the embodiment shown here, the partial image data f_j is therefore determined from a sector of one-dimensional Fourier spectra. Therefore, the temporal control point t_j of the sector can also be unambiguously defined according to the projection data assigned thereto. The mask, i.e. the filter function, can therefore determine the temporal control point t_j, in particular in the form of the temporal focus. Finally, FIG. 4d) shows the partial image data f_j according to the Fourier transformation of the masked frequency spectrum into the spatial domain.

The individual steps of the method according to an embodiment of the invention do not necessarily have to be carried out in the sequence described here. Rather it will be obvious to the average person skilled in the art that the sequence of the steps can be varied in so far as this is technically feasible.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a tangible computer readable medium and is adapted to perform any one of the aforementioned methods when run on a computer device (a device including a processor). Thus, the tangible storage medium or tangible computer readable medium, is adapted to store information and is adapted to interact with a data processing facility or computer device to execute the program of any of the above mentioned embodiments and/or to perform the method of any of the above mentioned embodiments.

The tangible computer readable medium or tangible storage medium may be a built-in medium installed inside a computer device main body or a removable tangible medium arranged so that it can be separated from the computer device main body. Examples of the built-in tangible medium include, but are not limited to, rewriteable non-volatile memories, such as ROMs and flash memories, and hard disks. Examples of the removable tangible medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Although the invention has been illustrated and described in greater detail by the preferred example embodiment, the invention is not restricted by the disclosed examples and other variations can be derived therefrom by the person skilled in the art, without departing from the scope of protection of the invention.

What is claimed is:

1. A method for motion compensation of image data of a moving scanned object, the image data being a spatially three-dimensional reconstruction from scan data and the scan data being acquired during a relative rotational movement between a radiation source and the scanned object within an angular range, wherein the angular range includes a plurality of angular sub-ranges, each angular sub-range being assigned to a temporal control point, said method comprising:
   (i) determining at least one value for an image metric of the image data, the image metric being a measure of motion artifacts in the image data;
   (ii) determining partial image data, the respective partial image data corresponding to respective spatially three-dimensional reconstruction from scan data of an angular sub-range;
   (iii) determining a respective motion field of the image data at a respective control point via an optimization method as a function of the image metric, wherein the respective motion field is a measure of respective motion of the image data;
   (iv) transforming the respective partial image data according to the motion described by the respective motion field; and
   (v) generating image data by merging the transformed respective partial image data, wherein the (i) to (v) are performed iteratively until a stop criterion is reached.

2. The method of claim 1, wherein the angular range is a minimum angular range necessary for a tomographically complete reconstruction.

3. The method of claim 1, wherein the partial image data is determined by at least:

fourier transformimg the image data into the frequency domain;
masking the frequency spectrum of the image data via a filter function; and
fourier transforming the masked frequency spectrum into a spatial domain.

4. The method of claim 1, wherein the respective partial image data is determined by forward projection of the image data and subsequent back projection of part of the projected image data corresponding to an angular sub-range.

5. The method of claim 1, comprising:
   (vi) forward projecting the image data with subsequent motion-compensated back projection via the respective at least one motion field.

6. The method of claim 1, wherein the image data is the image data of a segmented scanned object.

7. The method of claim 1, wherein the scanned object is at least one of at least one part of a heart and at least one coronary vessel.

8. The method of claim 1, wherein the value of the image metric is determined for each individual image slice from the image data.

9. The method of claim 1, wherein the image metric is one of the following image parameters:
   entropy,
   positivity,
   compressibility, or
   total variation.

10. The method of claim 1, wherein the optimization method for determining the at least one respective motion field is a gradient descent method, wherein the gradients $\partial L(s)/\partial s$ are determined in an image-based manner.

11. The method of claim 1, wherein the respective motion field for transforming the respective partial image data is interpolated between the control points.

12. A non-transitory computer readable medium storing a computer program that, when executed on b a processor, configures the processor to execute the method as claimed in claim 1.

13. A computer for image processing, comprising:
   a memory for storing a computer program; and
   a processor for executing the stored computer program, wherein processor is configured to carry out the method of claim 1 when the computer program is executed by the processor.

14. A computed tomography system, comprising:
   a radiation source;
   a radiation detector to interact with the radiation source and designed to acquire scan data during a relative rotational movement between the radiation source and a scanned object within an angular range;
   a reconstruction unit, designed to reconstruct image data from the scan data; and
   the computer for image processing of claim 13.

15. The method of claim 2, wherein the partial image data is determined by at least:
   fourier transformimg the image data into the frequency domain;
   masking the frequency spectrum of the image data via a filter function; and
   fourier transforming the masked frequency spectrum into a spatial domain.

16. The method of claim 2, wherein the respective partial image data is determined by forward projection of the image data and subsequent back projection of part of the projected image data corresponding to an angular sub-range.

17. The method of claim 2, wherein the image data is the image data of a segmented scanned object.

18. The method of claim 2, wherein the scanned object is at least one of at least one part of a heart and at least one coronary vessel.

19. A non-transitory computer readable medium comprising program segments for executing, when the computer program is executed by a processing unit of an imaging system, the method of claim 1.

* * * * *